(12) United States Patent
Goto

(10) Patent No.: US 7,088,386 B2
(45) Date of Patent: Aug. 8, 2006

(54) MAKEUP COUNSELING APPARATUS

(75) Inventor: Yasuo Goto, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 850 days.

(21) Appl. No.: 10/018,756

(22) PCT Filed: Apr. 19, 2001

(86) PCT No.: PCT/JP01/03342

§ 371 (c)(1),
(2), (4) Date: Dec. 17, 2001

(87) PCT Pub. No.: WO01/82154

PCT Pub. Date: Nov. 1, 2001

(65) Prior Publication Data

US 2003/0007071 A1    Jan. 9, 2003

(30) Foreign Application Priority Data

Apr. 21, 2000 (JP) .......................... 2000-121647
Apr. 21, 2000 (JP) .......................... 2000-121648

(51) Int. Cl.
*H04N 7/18* (2006.01)
*H04N 7/14* (2006.01)
*H04N 5/225* (2006.01)

(52) U.S. Cl. ...................... 348/77; 348/373; 348/14.07

(58) Field of Classification Search ............ 348/14.03, 348/14.07, 61, 77, 373
See application file for complete search history.

(56) References Cited

U.S. PATENT DOCUMENTS

| 4,903,136 A | 2/1990 | Iketani |
| 5,142,359 A | 8/1992 | Yamamori |
| 5,327,226 A | 7/1994 | Tanabe |
| 5,500,671 A * | 3/1996 | Andersson et al. ........ 348/14.1 |
| 5,579,031 A | 11/1996 | Liang |
| 5,657,246 A * | 8/1997 | Hogan et al. ............... 348/14.1 |
| 5,852,675 A | 12/1998 | Matsuo et al. |
| 5,920,342 A * | 7/1999 | Umeda et al. ......... 348/211.14 |
| 6,592,223 B1 * | 7/2003 | Stern et al. .................. 351/239 |
| 2002/0071246 A1 * | 6/2002 | Stewart ....................... 361/681 |

FOREIGN PATENT DOCUMENTS

| DE | 19616029 | 11/1997 |
| EP | 0981790 | 3/2000 |
| JP | 04279915 | 10/1992 |
| JP | 7067721 | 3/1995 |
| JP | 95164 | 1/1997 |
| JP | 10075458 | 3/1998 |
| JP | 10083421 | 3/1998 |
| JP | 11190979 | 7/1999 |

(Continued)

*Primary Examiner*—Lin Ye
(74) *Attorney, Agent, or Firm*—Ladas & Parry LLP

(57) ABSTRACT

The present invention is composed of a computer positioned at a basal portion of an apparatus for conducting image processing and counseling processing; a first image display means for displaying a computer-processed image to a subject, mounted upright in the computer, a second image display means for displaying the computer-processed image to a counselor, mounted upright in the computer so that a display screen thereof is directed in a direction opposite the first display means; and photographic means, positioned near the first image display means, for photographing a subject directed in a direction of the first display means and feeding a facial image of the subject into the computer, thus making the apparatus small in scale and simple in composition, and suitable for a counselor to provide counseling on make-up to a subject.

7 Claims, 7 Drawing Sheets

FOREIGN PATENT DOCUMENTS

| | | | | | |
|---|---|---|---|---|---|
| JP | 2000004939 | 1/2000 | WO | WO97/44642 | 11/1997 |

\* cited by examiner

| REDDISH SKIN COLOR | STANDARD SKIN COLOR | YELLOWISH SKIN COLOR | BLACKISH-RED SKIN COLOR | BLACKISH SKIN COLOR | BLACKISH-YELLOW SKIN COLOR |
|---|---|---|---|---|---|
| | | | WHITISH-RED SKIN COLOR | WHITISH SKIN COLOR | WHITISH-YELLOW SKIN COLOR |
| RED | GREEN | BLUE | | | |
| BLACK | N3.5 | N5 | N6.5 | N8 | WHITE |

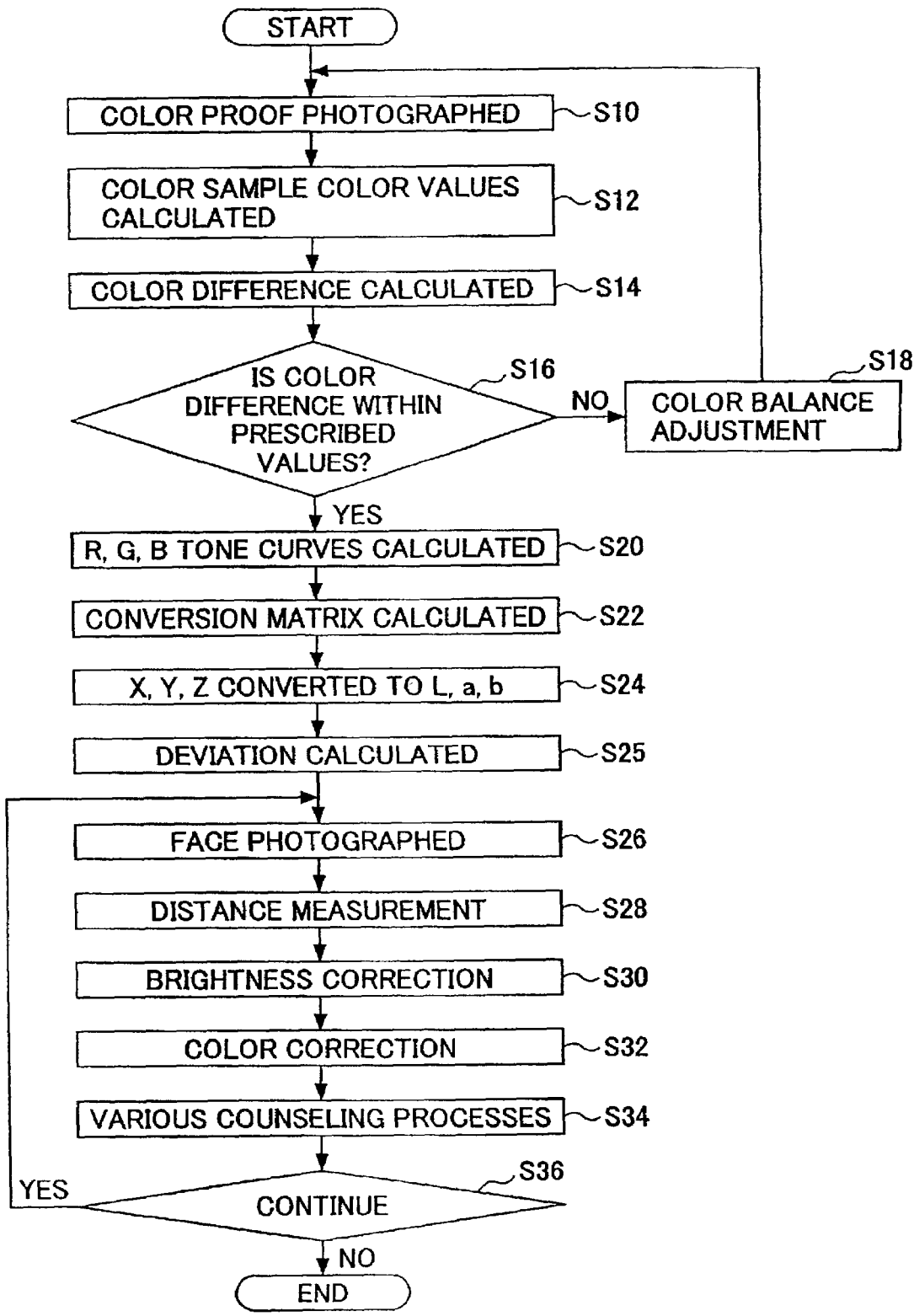

MAKEUP COUNSELING APPARATUS

TECHNICAL FIELD

The present invention relates to a make-up counseling apparatus, and more particularly, to a make-up counseling apparatus designed to be used for counseling make-up for a subject by acquiring a facial image of the subject.

BACKGROUND ART

When providing counseling on make-up, in order to select colors of lipstick and other cosmetics that match that person's skin color, it is necessary to have an accurate understanding of skin color.

In Japanese Laid-Open Patent Application No. 10-174733, the present applicant has proposed a system for providing make-up counseling by measuring and classifying the color of the skin of a person's face and acquiring a facial image. In this system, a strobe and digital camera, as well as a halogen lamp for spectral measurements, are provided inside a measurement unit. The measurement unit is then positioned at a predetermined distance from a chair in which the subject sits. A half mirror is provided at the front of the measurement unit, and the subject's posture is then adjusted so that the center of the face aligns with a reference line inscribed on the half mirror and indicating the photographic center. The skin color is measured by analyzing the reflected light with a spectrometer at the same time as other processes are carried out as well.

The conventional measurement unit is an elaborate affair, having a half mirror on the front and containing a strobe and camera as well as a halogen lamp and a spectrometer. The large scale and the cost of such apparatuses were drawbacks.

In reducing the scale of the system, it might appear that the halogen lamp and the spectrometer can be eliminated and skin color measurement obtained easily from the facial image as photographed by the digital camera. However, the luminance and the color of the facial image changes due to the effects of external light from the environment in which the system is located, and moreover, fluctuations in the distance from the digital camera to the subject causes the luminance of the facial image to change, resulting in the problem that the skin color cannot be measured accurately, that is, without being affected by the environment.

DISCLOSURE OF THE INVENTION

It is a general object of the present invention to provide an improved and useful make-up counseling apparatus that solves the above-described problems of the conventional art.

A more specific object of the present invention is to provide a make-up counseling apparatus that is small in scale and simple in structure, and suitable for a counselor to provide counseling on make-up to a subject.

Another object of the present invention is to provide a make-up counseling apparatus that is small in scale and simple in structure, and further, that can objectively and accurately measure the brightness and skin color of a subject's face.

In order to achieve these objects, the present invention comprises a computer positioned at a basal portion of an apparatus for conducting image processing and counseling processing; a first image display means for displaying a computer-processed image to a subject, mounted upright in the computer; a second image display means for displaying the computer-processed image to a counselor, mounted upright in the computer so that a display screen thereof is directed in a direction opposite the first display means; and photographic means, positioned near the first image display means, for photographing a subject directed in a direction of the first display means and feeding a facial image of the subject into the computer.

According to such a make-up counseling apparatus, because a first and second image display means are provided upright on a computer and a photographic means is provided nearby, the scale of the apparatus can be reduced and its structure can be simplified.

In order to achieve these objects, the present invention further comprises a make-up counseling apparatus comprising a digital camera for photographing a subject; a strobe for illuminating the subject; a distance sensor for measuring a distance to the subject; color balance adjustment means for adjusting a color balance of the digital camera so that a difference in color between color values of a color sample image of predetermined colors obtained from a color correction chart having a plurality of color samples placed at approximately equal distances illuminated by the strobe light and photographed by the digital camera, and color values of color samples of the predetermined colors measured under previously predetermined conditions is within a stipulated range of values; conversion formula calculation means for obtaining a conversion formula for converting the color values of the color sample image obtained from photographing the color correction chart with the digital camera into Lab values of the color samples measured under previously predetermined conditions; deviation calculation means for obtaining a deviation between the color values of the color sample image obtained from photographing the color correction chart with the digital camera converted into Lab values using the conversion formula and the Lab values of color samples of the predetermined color measured under previously predetermined conditions; brightness correction means for correcting the brightness of a facial image according to a distance measured by the distance sensor when the facial image of a subject at approximately a fixed distance is photographed by the digital camera as a photographic object; and color correction means for correcting the brightness-corrected facial image according to the deviation.

According to such a make-up counseling apparatus, by adjusting the color balance of the digital camera using the color correction chart, obtaining a conversion equation for converting the image photographed with the digital camera into Lab values, obtaining a deviation thereof with respect to a reference of an image photographed using the digital camera, correcting a brightness of the facial image of the subject according to the distance measured by the distance sensor, and further correcting the color of the facial image by the aforementioned deviation, the brightness and skin color of the face of the subject can be measured accurately without being affected by the environment using a simple composition of the digital camera, the strobe and the distance sensor.

BRIEF DESCRIPTION OF THE DRAWINGS

Other objects, features and advantages of the present invention will become more apparent from the following detailed description and the accompanying drawings.

FIG. 6 is a diagram showing one embodiment of a color correction chart 75.

FIG. 7 is a main flow chart of one embodiment of processes executed by the apparatus of the present invention.

BEST EMBODIMENT FOR PRACTICING THE INVENTION

A description is given below of an embodiment of the present invention, based on the drawings.

Figure 1:
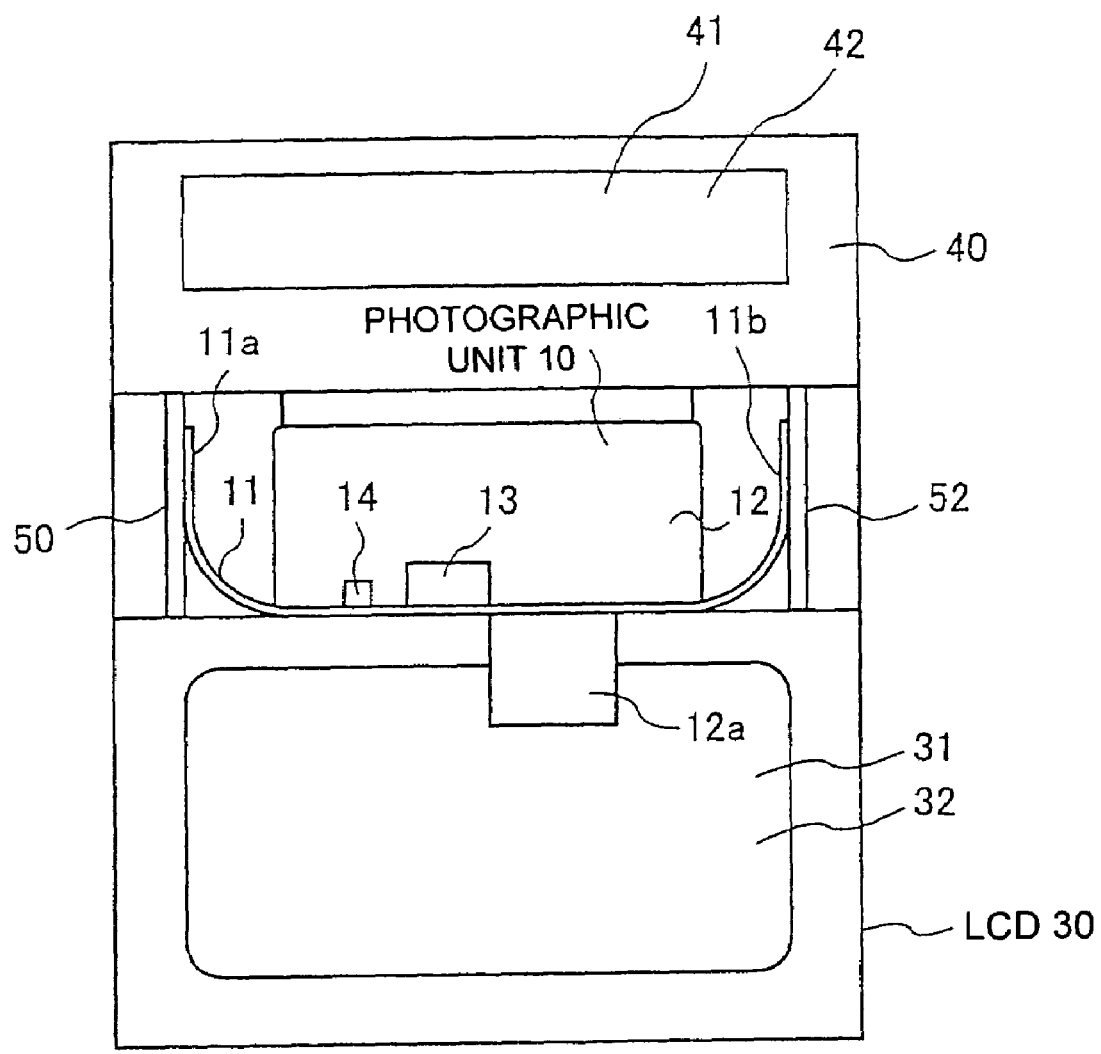
FIG. 1 is a plan view of one embodiment of the make-up counseling apparatus of the present invention.
Figure 2:
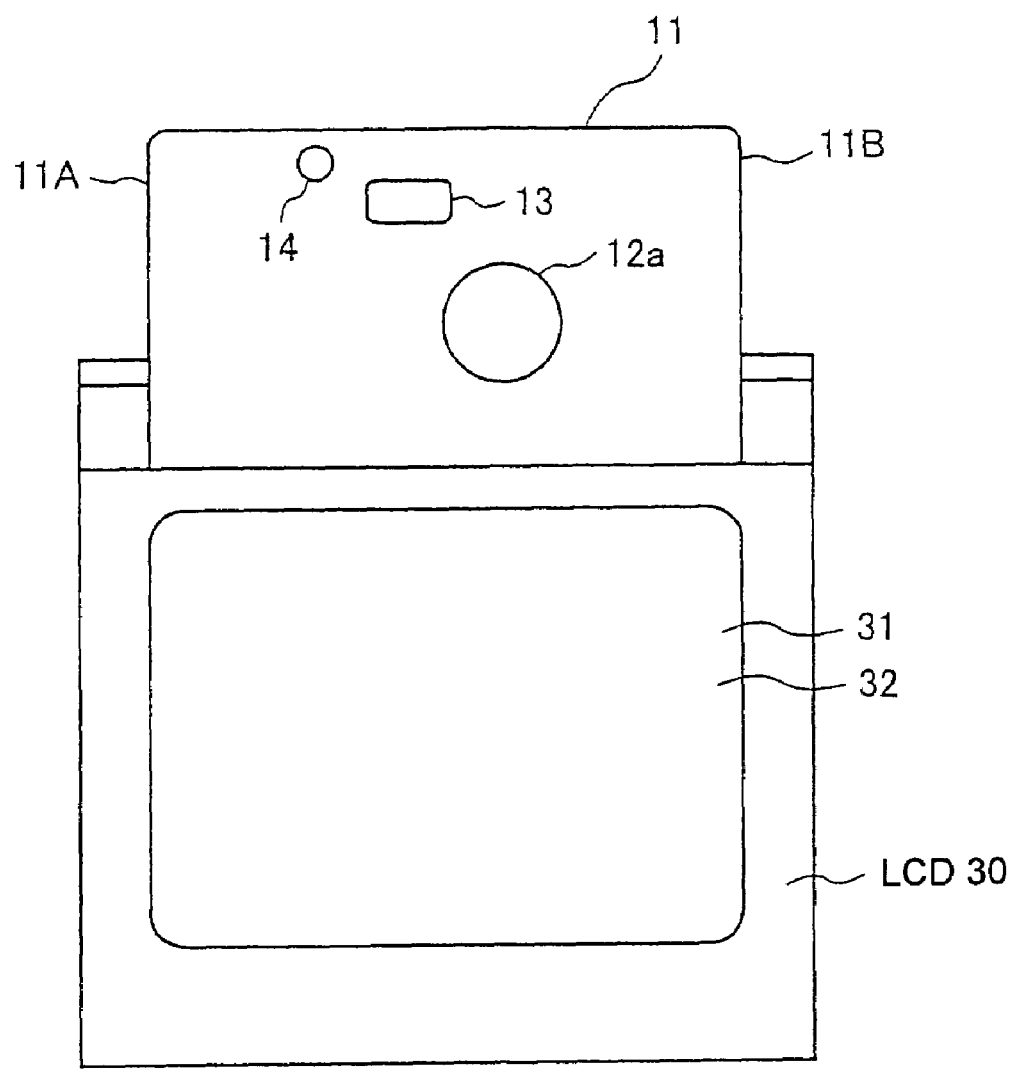
FIG. 2 is a front view of one embodiment of the make-up counseling apparatus of the present invention.
Figure 3:
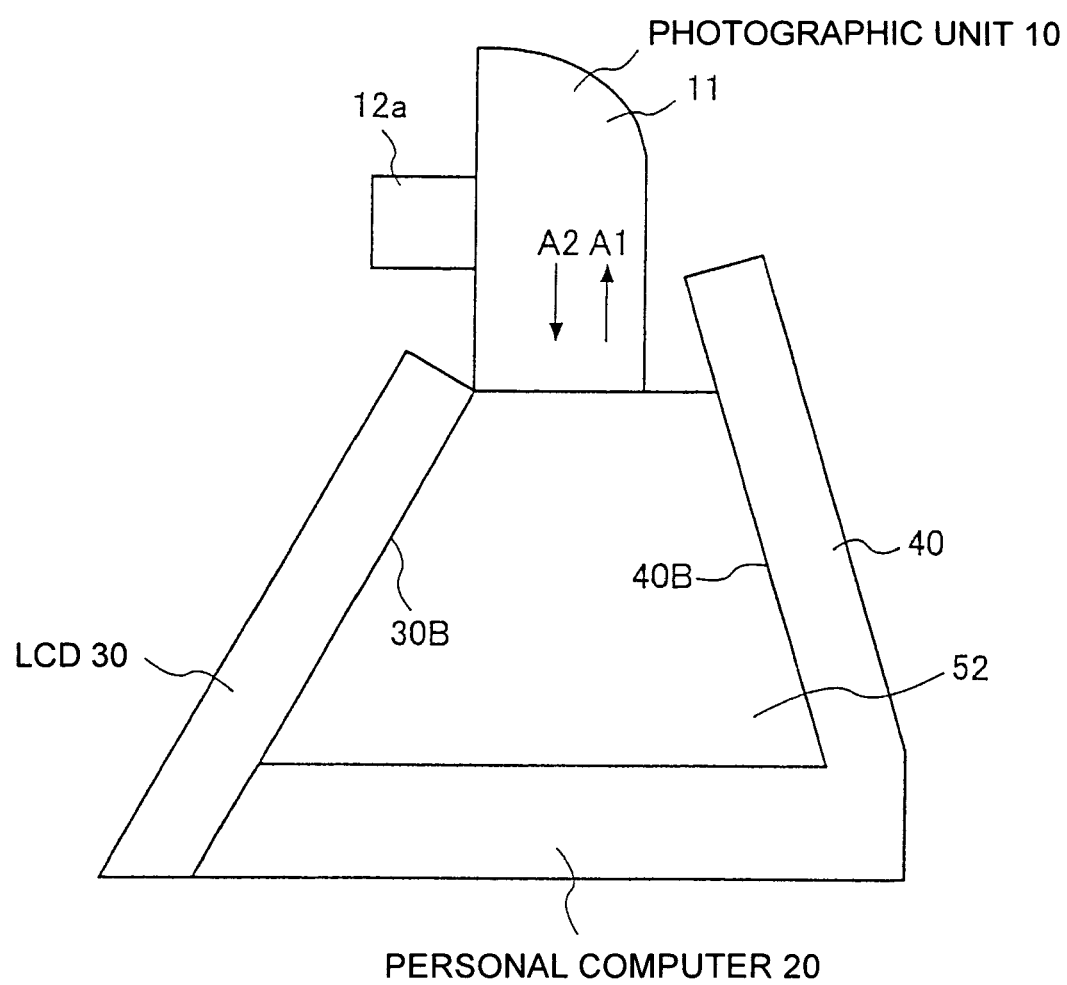
FIG. 3 is a side view of one embodiment of the make-up counseling apparatus of the present invention.

FIG. 1, FIG. 2 and FIG. 3 show plan, front and side views of the make-up counseling apparatus of the present invention. In FIGS. 1–3, the make-up counseling apparatus comprises a photographic unit 10, a personal computer 20, a liquid crystal display (LCD) monitor 30 with a touch panel for use by a subject, and a LCD monitor 40 with a touch panel for use by a counselor.

The personal computer 20 is positioned at the bottom of a base of the apparatus, and as shown in FIG. 3 the LCD monitors 30 and 40 are positioned upright along two parallel sides of the personal computer 20 so that their rear surfaces are disposed opposite each other and inclined so that their upper edges contact each other. Acrylic trapezoidal side panel members 50, 52 are positioned upright along both left and right edges as shown in FIG. 1. These side panel members 50, 52 are fixedly mounted on the personal computer 20 and the LCD monitors 30 and 40, respectively, forming a storage space for the photographic unit 10.

The photographic unit 10 comprises an acrylic face member 11 that is U-shaped in cross-section, a digital camera 12, a strobe 13 and a distance sensor 14, each fixedly mounted. A lens 12a of the digital camera 12 projects from the face member 11, with through-holes provided on the face member 11 for positioning light from the strobe 13 and for positioning input/output of ultrasound (or electromagnetic) waves from the distance sensor 14, respectively.

The photographic unit 10 is installed by left and right edges 11a, 11b of the face member 11 with the U-shaped cross-section being guided by the side panel members 50, 52 so as to slide freely in the direction of arrows A1, A2 as shown in FIG. 3, and in the state shown in FIG. 3 retaining parts of the face member 11 which are not shown in the drawing engage the side panel members 50, 52. Similarly, when the lens 12a is retracted into the camera 12 and stored and the above-described engagement is released, the photographic unit 10 becomes slidable. The photographic unit 10 can then be slid in the direction of arrow A2 and stored in the above-described storage space.

The LCD monitor 30 with a touch panel for use by the subject is configured so that a transparent touch panel 32 is adhered atop the entire surface of a LCD unit 31. The LCD monitor 40 with a touch panel for use by a counselor is similarly configured, with a transparent touch panel 42 adhered atop the entire surface of a LCD unit 41. It should be noted that the respective LCD units 31, 41 of the LCD monitors 30, 40 are disposed so as to face in opposite directions.

Figure 4:
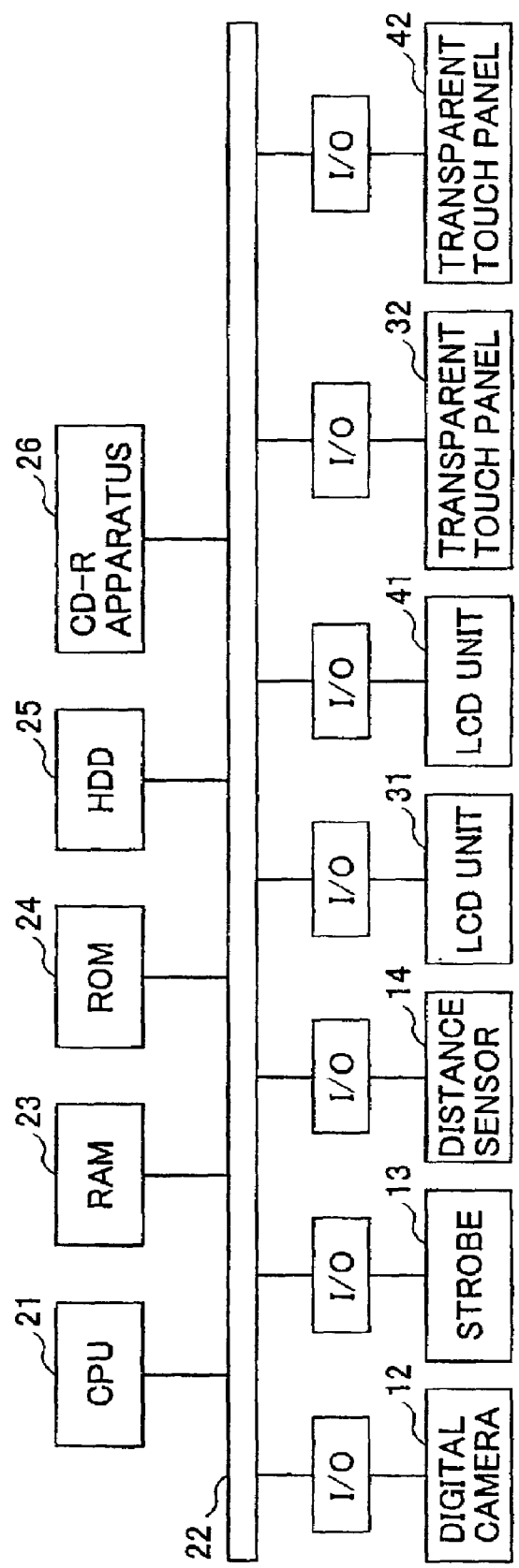
FIG. 4 is a block diagram of one embodiment of the make-up counseling apparatus of the present invention.

FIG. 4 is a block diagram of one embodiment of the make-up counseling apparatus of the present invention. In the diagram, in the personal computer 20 a central processing unit (CPU) 21 is connected to a RAM 23, a ROM 24, a hard disk drive (HDD) 25 and a CD-R (compact disk-recordable) device 26, respectively, via a bus 22. Additionally, the digital camera 12, strobe 13 and distance sensor 14 of the photographic unit 10 as well as the LCD units 31, 41 and transparent touch panels 32, 42 of the LCD monitors 30, 40 are connected via an I/O interface (I/O). It should be noted that it is permissible to use a storage medium such as a floppy disk, CD-RW or MO and the like in place of the CD-R.

The CPU 21 executes a variety of processing programs stored in the ROM 24 or the hard disk 25, and proceeds with processing in response to input from the transparent touch panels 32, 42. Additionally, processing results are written to the CD-RW device 26 and at the same time displayed by the LCD units 31, 41, respectively.

Figure 5:
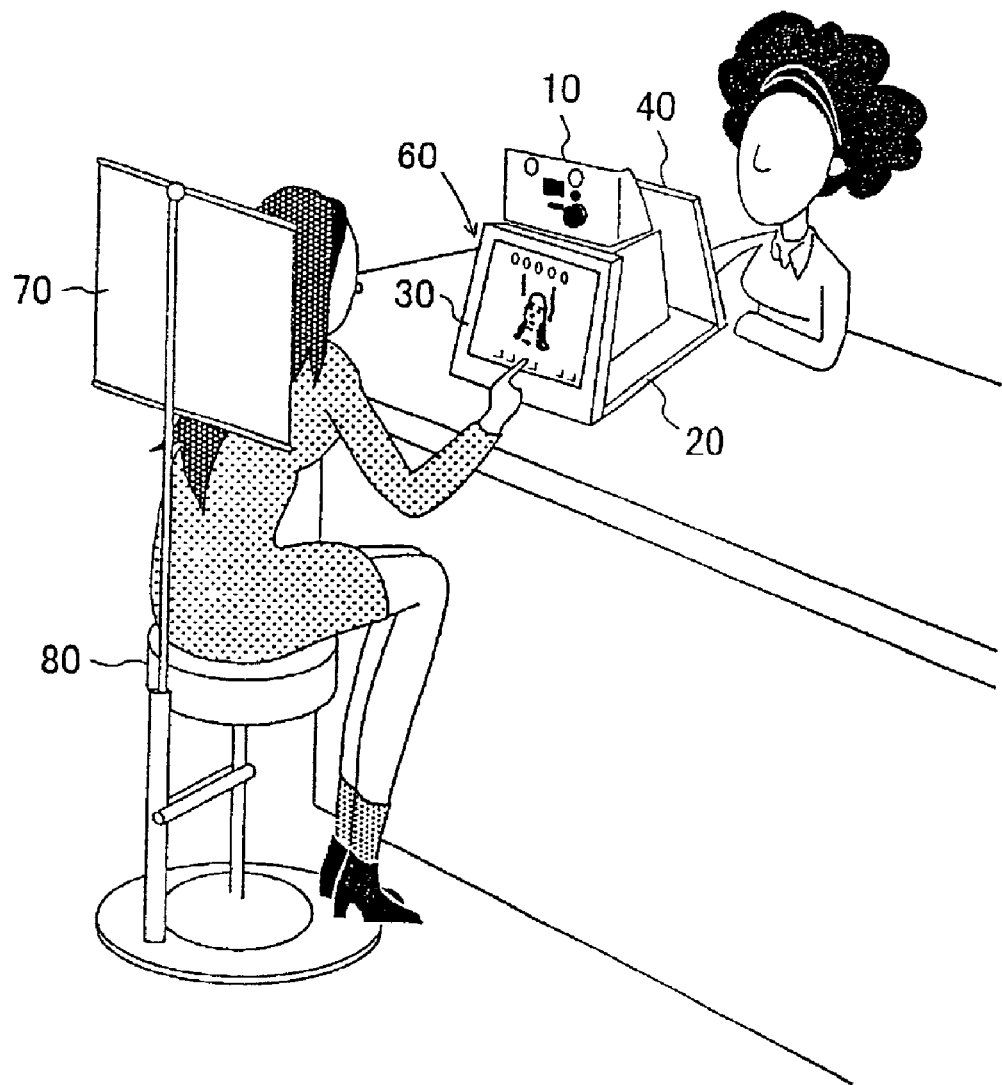
FIG. 5 is a diagram showing the make-up counseling apparatus of the present invention in use.

FIG. 5 is a diagram showing the make-up counseling apparatus of the present invention in use. In the diagram, a make-up counseling apparatus 60 is placed on top of a desk. The subject sits in a chair 80 with her back toward a background screen 70, directly facing the photographic unit 10 of the make-up counseling apparatus 60. In this state the subject's face is photographed by the digital camera 12. The subject then talks with the counselor across the make-up counseling apparatus 60.

When correcting the photographic unit 10, a color correction chart 75 is provided at a position at which the face is photographed on the background screen 70 facing the digital camera 12 as shown in FIG. 6. On the color correction chart 75 are printed a variety of color samples, from reddish skin color to standard skin color, yellowish skin color, blackish-red skin color, blackish skin color, blackish yellow skin color, red, green blue, whitish red skin color, whitish skin color, whitish yellow skin color, black, color number N3.5, color number N5, color number N6.5, color number N8 and white. It should be noted that the color numbers N3.5, N5, N6.5 and N8 are respectively N3.5, N5, N6.5 and N8 grays on the lightness scale of the Munsell value function.

FIG. 7 is a main flow chart of one embodiment of processes executed by the apparatus of the present invention. First, as a preprocessing for acquiring a facial image, in a step S10 the strobe 13 is fired, the color correction chart 75 of the background screen 70 is photographed by the digital camera 12, and in a step S12 the color value of the color sample of each and every color inside the color correction image (the average value of a plurality of picture elements) is obtained. Next, in a step S14, a color difference between the color value of the standard skin color of the color correction chart image and the color value of the standard skin color previously stored in the hard disk drive 25 is obtained. In a step S16 it is determined whether or not the color difference is within prescribed values and, if outside those limits, then in a step S18 the color balance of the digital camera 12 is adjusted so as to minimize the above color difference. The process then proceeds to the step S10, where steps S10–S18 are repeated.

If in step S16 it is determined that the above-described color difference is within prescribed limits, then the process proceeds to a step S20, where the respective color values R, G, B of the gray chip black, color number N3.5, color number N5, color number N6.5, color number N8 and white within the color correction chart image undergo linear conversion to obtain the red TRC, green TRC and blue TRC tone curves of the luminance corresponding to red, green and blue. Next, in a step S22, red TRC(R), green TRC(G) and blue TRC(B), which are values obtained by linear conversion of color values R, G, and B for each of reddish skin color, standard skin color and yellowish skin color within the color correction chart image with the tone curves red TRC(R), green TRC(G) and blue TRC(B), and the CIE (Commission Internationale de l'Éclairage) 3 stimulus values XYZ of the reddish skin color, standard skin color and yellowish skin color previously stored in the hard disk drive 25, are substituted into formula (1) below and individual conversion matrix elements rXc, rYc, rZc, gXc, gYc, gZc, bXc, bYc, bZc are obtained.

(Formula 1)

Next, in a step S24, using the formula (1) that used the obtained conversion matrix, the reddish skin color, standard skin color and yellowish skin color within the color correction chart are each converted to CIE 3 stimulus values XYZ, and the respective CIE 3 stimulus values XYZ of the reddish skin color, standard skin color and yellowish skin color are converted to Lab values using a formula (2). It should be noted that the Lab values are a color space expressed as metric lightness (L), metric hue angle (a) and metric chroma (b).

$$a = 17.5(1.02X-Y)/\sqrt{Y}$$

$$b = 7.0(Y-0.84Z)/\sqrt{Y}$$

$$L = 10\sqrt{Y}, \quad 0 < Y < 100 \quad (2)$$

Next, in a step S25, the color correction chart 75 is once more photographed with the digital camera 12, the L,a,b values obtained for each of the reddish skin color, standard skin color and yellowish skin color within the color correction chart image and the deviation thereof from the respective L,a,b values for the reddish skin color, standard skin color and yellowish skin color measured by the spectrometer and previously stored in the hard disk drive 25 is stored in the hard disk drive 25.

Thereafter, in a step S26, the strobe 13 fires and the face of the subject sitting in the chair 80 with the background screen 70 as a background is photographed with the digital camera 12. Virtually simultaneously, in a step S28 the distance to the subject's face is measured by the distance sensor 14.

Next, in a step S30, the luminance of the facial image of the subject is revised in picture element units, based on the measured distance. If the distance measured by the distance sensor 14 is D1 with respect to a given reference photograph distance D and a luminance correction factor k=(D1/D)2 is obtained and the CIE 3 stimulus values of the facial image of the subject are X1, Y1, Z1, then the CIE 3 stimulus values X, Y Z of the facial image at the reference photograph distance D are obtained according to formula (3).

$$X = k \times X1$$

$$Y = k \times Y1$$

$$Z = k \times Z1 \quad (3)$$

Thereafter, in a step S32, the facial image is color corrected using the deviation obtained previously in the step S24. Thereafter, in a step S34, various counseling processes are conducted using the corrected facial image to determine skin color distribution over the entire face, determine a facial look, carry out simulations involving different lipstick, eye shadow, eye liner, rouge, hairstyles and so forth, thereby providing make-up counseling to the subject.

Thereafter, in a step S36, it is determined whether or not to continue with the processing. If continued, then the process proceeds to a step S26 and repeats steps S26–S36. If not continued, then the process is terminated.

As described above, LCD monitors 30, 40 are supplied upright on a personal computer 20 and a photographic unit 10 is positioned nearby, so the scale of the apparatus can be reduced and its structure simplified. Additionally, the space formed by the personal computer 20 and the LCD monitors 30, 40 is used as container space for the photographic unit 10, thus making it possible to make the apparatus even more compact, and in particular, improving the portability of the apparatus. Additionally, the use of LCD monitors 30, 40 with touch panels makes an input apparatus such as a keyboard unnecessary, making it possible to make the make-up counseling apparatus even more compact.

Additionally, because the photographic unit 10 has the digital camera 12 for taking photographs of the subject, the strobe 13 for illuminating the subject and the distance sensor 14 for measuring a distance to the subject, luminance correction of the image of the subject photographed can be corrected based on the distance to the subject.

Additionally, by adjusting the color balance of the digital camera 12 using the color correction chart 75, obtaining a conversion equation for converting the image photographed with the digital camera 12 into Lab values, obtaining a deviation thereof with respect to a reference of an image photographed using the digital camera, correcting a brightness of the facial image of the subject according to the distance measured by the distance sensor 14, and further correcting the color of the facial image by the aforementioned deviation, the brightness and skin color of the face of the subject can be measured accurately without being affected by the environment using a simple composition of the digital camera 12, the strobe 13 and the distance sensor 14.

Moreover, as shown in the use embodiment in FIG. 5, the respective LCD units 31, 41 of the LCD monitors 30, 40 are disposed so as to face in opposite directions, so the counselor can dispense counseling by facing the subject directly while the subject looks at the LCD unit 31 and the counselor looks at the LCD unit 41. At this time, the contents of the display displayed by the LCD unit 31 and the contents of the display displayed by the LCD unit 41 may be the same. However, for the LCD unit 41 comments for counseling use may be added to the display contents of the LCD unit 31, or the contents of the two displays may be completely different.

It should be noted that the photographic unit 10 corresponds to the photographic means of the claims, the LCD monitor 30 with a touch panel for use by a subject corresponds to the first image display means, the LCD monitor 40 with a touch panel for use by a counselor corresponds to the second image display means, steps S1–0S18 correspond to the color balance adjustment means, steps S20–S22 correspond to the conversion formula calculation means, steps S24 and S25 correspond to the deviation calculation means, step S30 corresponds to the brightness correction means and step S32 corresponds to the color correction means.

What is claimed is:

1. A make-up counseling apparatus comprising:
   a computer positioned at a basal portion of the apparatus for conducting image processing and make-up counseling processing for make-up of a subject's face;
   a first image display means for displaying a computer-processed image of the subject's face to a subject, mounted upright in the computer;
   a second image display means for displaying the computer-processed image of the subject's face to a counselor, mounted upright in the computer so that a display screen thereof is directed in a direction opposite the first display means; and photographic means, positioned near the first image display means, for photographing the subject's face directed in a direction of the first display means and feeding a facial image of the subject's face into the computer.

2. The make-up counseling apparatus as claimed in claim 1, wherein a space bounded by the computer and by the first and second image display means contains the photographic means.

3. The make-up counseling apparatus as claimed in claim 1, wherein the photographic means comprises:
- a digital camera for photographing the subject's face;
- a strobe for illuminating the subject's face; and
- a distance sensor for measuring a distance to the subject's face.

4. The make-up counseling apparatus as claimed in claim 1, wherein the first image display means has a transparent touch panel on the display surface.

5. The make-up counseling apparatus as claimed in claim 1, wherein the second image display means has a transparent touch panel on the display surface.

6. The make-up counseling apparatus as claimed in claim 1, wherein display contents of the first image display means and display contents of the second image display means are identical.

7. The make-up counseling apparatus as claimed in claim 1, wherein the display contents of the first image display means and the display contents of the second image display means are different.

* * * * *